(12) United States Patent
Mabondzo et al.

(10) Patent No.: US 12,403,113 B2
(45) Date of Patent: Sep. 2, 2025

(54) COMPOSITION CONTAINING CREATINE FATTY ESTER FOR USE IN MEDICINE

(71) Applicant: COMMISSARIAT À L'ÉNERGIE ATOMIQUE ET AUX ÉNERGIES ALTERNATIVES, Paris (FR)

(72) Inventors: Aloïse Mabondzo, Paris (FR); Gabriela Ullio-Gamboa, GIF s/ Yvette (FR); Anne-Cécile Guyot, Rueilmalmaison (FR); Sophie Dezard, Forges les Bains (FR); Frédéric Taran, GIF s/ Yvette (FR); Henri Benech, Paris (FR); Olivier Loreau, St Michel s/ Orge (FR)

(73) Assignee: COMMISSARIAT À L'ÉNERGIE ATOMIQUE ET AUX ÉNERGIES ALTERNATIVES, Paris (FR)

(*) Notice: Subject to any disclaimer, the term of this patent is extended or adjusted under 35 U.S.C. 154(b) by 976 days.

(21) Appl. No.: 17/594,629

(22) PCT Filed: Apr. 29, 2020

(86) PCT No.: PCT/EP2020/061824
§ 371 (c)(1),
(2) Date: Oct. 25, 2021

(87) PCT Pub. No.: WO2020/221780
PCT Pub. Date: Nov. 5, 2020

(65) Prior Publication Data
US 2022/0211651 A1    Jul. 7, 2022

(30) Foreign Application Priority Data

Apr. 30, 2019 (EP) ..................................... 19305548

(51) Int. Cl.
*A61K 31/201* (2006.01)
*A61K 31/202* (2006.01)
(Continued)

(52) U.S. Cl.
CPC .......... *A61K 31/201* (2013.01); *A61K 31/202* (2013.01); *A61K 45/06* (2013.01); *A61P 25/00* (2018.01)

(58) Field of Classification Search
CPC ...... A61K 31/201; A61K 31/20; A61K 45/06; A61K 31/513; A61P 25/00; A61P 21/00; A23L 33/12; A23L 33/175
See application file for complete search history.

(56) References Cited

U.S. PATENT DOCUMENTS

| | | | |
|---|---|---|---|
| 2002/0049253 A1 | 4/2002 | Kaddurah-Daouk | |
| 2003/0212130 A1 | 11/2003 | Miller et al. | |

(Continued)

FOREIGN PATENT DOCUMENTS

| | | |
|---|---|---|
| EP | 0589843 B1 | 11/2011 |
| EP | 2692719 B1 | 6/2016 |

(Continued)

OTHER PUBLICATIONS

Trotier-Faurion et al., Nanomedecine, 2015, 10(2), 185-191. (Year: 2015).*

(Continued)

*Primary Examiner* — Deborah D Carr
(74) *Attorney, Agent, or Firm* — Chrisman Gallo Tochtrop LLC (57) ABSTRACT

A composition comprising at least one creatine fatty ester or salt thereof, at least one omega 3 fatty acid or salt thereof and at least one glyceride for use in medicine, the composition being free of non ionic surfactants and in particular (Continued)

said composition for use in treating the brain creatine transporter deficiency disease.

13 Claims, 1 Drawing Sheet

(51) Int. Cl.
*A61K 45/06* (2006.01)
*A61P 25/00* (2006.01)

(56) References Cited

U.S. PATENT DOCUMENTS

2015/0238453 A1 8/2015 Owoc
2021/0128467 A1 5/2021 Mabondzo

FOREIGN PATENT DOCUMENTS

WO 0222135 A1 3/2002
WO WO-2015120299 A1 * 8/2015 ............. A23L 33/10

OTHER PUBLICATIONS

Trotier-Faurion, PHD Thesis, 2013, Univ. Paris-Sud. (Year: 2013).*
Stockler, Sylvia et al, "Cerebral creatine deficiency syndromes. Clinical aspects, treatment and pathophysiology", Subcell. Biochem., 2007, vol. 46, pp. 149-166.
Green, Douglas R et al. "Mitochondria and the autophagy-inflammation-cell death axis in organismal aging" Science. Aug. 26, 2011; vol. 333, 1109-1112.
Van De Kamp, Jiddeke M. et al "X-linked creatine transporter deficiency: clinical aspects and pathophysiology", J Inherit Metab Dis., 2014, vol. 37, pp. 715-733.
Kurosawa, Yuko et al, "Cyclocreatine treatment improves cognition in mice with creatine transporter deficiency", The Journal of CLinical Invenstigation, 2012, vol. 122(8), pp. 2837-2846.
Trotier-Faurion, Alexandra et al, Synthesis and biological evaluation of new creatine fatty esters revealed dodecyl creatine ester as a promising Nanomedicine, 2015 J. Med. Chem., vol. 56, pp. 5173-5181.
Trotier-Faurion, Alexandra et al, "Dodecyl creatine ester and lipid nanocapsule: a double strategy for the treatment of creatine transporter deficiency", Nanomedicine, 2013, vol. 10, pp. 185-191.
Banerjee, Bidisha et al, "Effect of creatine monohydrate in improving cellular energetics and muscle strength in ambulatory Duchenne muscular dystrophy patients: a randomized, placebo-controlled 31P MRS Study", 2010, Magnetic Resonance Imaging, vol. 28, pp. 698-707.
Balestrino, Maurizio et al, "Potential of creatine or phosphocreatine supplementation in cerebrovascular disease and in ischemic heart disease", 2016, Amino Acids, vol. 48, pp. 1955-1967.
Royes, Luiz Fernando Freire et al., 2016, "The effects of creatine supplementation and physical exercise on traumatic brain injury", Mini Review in Medicinal Chemistry, vol. 16, pp. 29-39.
Brewer, Gregory et al. "Protective effect of the energy precursor creatine against toxicity of glutamate and beta-amyloid in rat hippocampal neurons", Journal of Neurochemistry, 2000, vol. 74, pp. 1968-1978.
Lesman, M. et al, "Intracerebroventricular administration of creatine protects against damage by global cerebral ischemia in rat", Brain Res, 2006, vol. 1114, pp. 187-194.
Chaturvedi, Rajnish et al. "Mitochondrial approaches for neuroprotection", Annals od the New York Academy of Sciences, 2008, vol. 1147, pp. 395-412.
Abou-Sleiman, Patrick M. et al, "Expanding insights of mitochondrial dysfunction in Parkinson's disease", Nature Reviews/Neuroscience, Mar. 2006, vol. 7, pp. 207-219.
Matthews, Russell T. et al, "Creatine and cyclocreatine attenuate MPTP neurotoxicity", Exp Neurol, vJan. 19, vol. 157, pp. 142-149.
Adhihetty, Peter J. et al, "Creatine and its potential therapeutic value for targeting cellular energy impairment in neurodegenerative diseases", Neuromolecular Med, 2008, vol. 10, pp. 275-290.
Hersch, S.M. et al, 2006, "Creatine in Huntington disease is safe, tolerable, bioavailable in brain and reduces serum 8OH2'dG", Neurology, vol. 66, pp. 250-252.
Allen, Patricia J., "Creatine metabolism and psychiatric disorders: Does creatine supplementation have therapeutic value?", Neuroscience Biobehavioral Reviews, v2012, ol. 36, pp. 1442-1462.
Isper, Jonathan C. et al, "1H-MRS in autism spectrum disorders: a systematic meta-analysis", Metab Brain Dis, v2012, vol. 27, pp. 275-287.
Hoerst, Mareen et al, 2010, "Metabolic alterations in the amygdala in borderline personality disorder: a proton magnetic resonance spectroscopy study", Biol Psychiatry, vol. 67, pp. 399-405.
Bender, A. et al, 2008, "Creatine improves health and survival of mice", Neurobiology of Aging, vol. 29, pp. 1404-1411.
Skelton, Matthew R.et al, "Creatine transporter (CrT; Slc6a8) knockout mice as a model of human CrT deficiency", PLoS One, Jan. 2011, vol. 6, e16187.
Search Report for European application No. EP19305548 dated Oct. 23, 2019.
International Search Report and Written Opinion for application No. PCT/EP2020/061824 dated Jul. 13, 2020.

* cited by examiner

COMPOSITION CONTAINING CREATINE FATTY ESTER FOR USE IN MEDICINE

CROSS-REFERENCE TO RELATED APPLICATIONS

This is a National Stage application of PCT international application PCT/EP2020/061824, filed on Apr. 29, 2020, which claims the priority of European Patent Application No. 19305548.0 filed Apr. 30, 2019, both of which are incorporated herein by reference in their entirety.

TECHNICAL FIELD

The present invention belongs to the general field of systems for administering active ingredients and more particularly a composition containing creatine derivatives such as creatine fatty esters and salts thereof.

The present invention concerns said composition for use in medicine and in particular in treating Creatine Transporter Deficiency (CTD) by nasal administration.

State of the Prior Art

Creatine (Cr) is an endogenous nutrient produced naturally by the liver and kidneys in most vertebrates. Creatine also known as 2-1(methylguanidino) acetic acid is represented by the following formula (I):

2-(1-methylguanidino) acetic acid (I)

Creatine can also be represented by the following formula (I'):

(I')

The uses of creatine are many, including use as supplement to increase muscle mass and enhance muscle performance as well as in emerging applications in the treatment of various disorders such as, without limitation, various neuromuscular disorders, hypoxia and ischemic brain diseases such as stroke, heart disease, various muscular dystrophies [1], various skin disorders [2] and inflammation [3].

In addition the International application WO 2015/120299 proposes a neutraceutical or pharmaceutical composition for treating depression and anxiety-related disorders by acting on the metabolic integrity and capacity of mitochondria [4]. This composition comprises (a) at least one creatine or creatine analog, (b) at least one omega-3 fatty acid such as, for example, docosahexaenoic acid (DHA) and (c) citicoline. Among the creatine analogs, creatine esters, in particular creatine alkyl esters and more particularly creatine ethyl ester are cited. The pharmaceutical compositions disclosed in [4] are suitable for oral, rectal, topical and parenteral administration.

The deficits of the metabolism of creatine, include enzymatic deficits of its biosynthesis (deficits in Arginine:Glycine AmidinoTransferase (AGAT) and GuanidinoAcetate MethylTransferase (GAMT) of recessive autosomic transmission) and of its intra-cerebral transport (gene SLC6A8/CT1, related to X chromosome). Indeed Creatine Transporter Deficiency (CTD) is an inherited neurological disease caused by impairment of a cellular creatine transporter. This disorder drastically affects brain function with intellectual disability being the main phenotypic outcome.

Creatine is essential for proper brain function, having a crucial role in energy storage and transmission, and additional roles as anti-apoptotic, anti-oxidant, neuroprotector and neuromodulator [5].

Moreover, mitochondria are small membrane enclosed organelles, mobile and plastic, associated with ATP generation, calcium regulation and the biosynthesis of aminoacids, lipids and nucleotides [6]. The location of mitochondria in the cell varies between cell types and they are localized closer sites of ATP demands as their major role is to produce and supply ATP energy to the cells, the enzyme complexes forming the respiratory chain. Electron flow through the electron transport chain generates a proton gradient across the inner mitochondrial membrane, which drives the production of ATP by ATP synthase. Mitochondria are highly important during brain development and throughout life in metabolic tasks for the regulation cell of deaths. Mitochondria are also able to converge signaling pathways involved in inflammation through for example mitochondrial ROS production.

Several mitochondria dysfunctions were tried to be cured with creatine salts given by the oral route. The results were often negative. It is worth noting that the creatine circulating into the blood cannot enter efficiently the brain due to the presence of the blood brain barrier and especially to the creatine transporter which is saturated at the physiological creatine blood concentrations. Thus, only a very small percentage of oral creatine supplementation can enter the brain. Moreover, several types of neurones in the brain do not express the creatine transporter and thus cannot assimilate creatine supplementation.

CTD is a very rare disease, with around 110 cases reported in Europe. In CTD, the defective gene (SLC6A8) encodes for the sodium and chloride dependent Creatine Transporter (CrT) whose function is to transport creatine into and out of cells. Insufficient creatine transportation in neuronal cells leads to impaired energy metabolism and possibly neurotransmission defect. It affects primarily the brain, and is mainly characterized by mental retardation, severe speech delay, autistic like behaviour, and seizures, although other symptoms may also be observed like failure to thrive, muscle hypotonia, neurologic and psychiatric complications, cardiac and intestine manifestations. As SLC6A8 deficiency is an X-linked disorder, mainly males are affected, while according to the X-inactivation pattern heterozygous females may have a variable clinical phenotype, with mild neuropsychologic impairment.

Different therapeutic approaches have been experimented worldwide to address the critical issue of absence of creatine in brain cells of CTD patients. Currently, none of these approaches has led to significant benefit for CTD patients. Indeed, administration of pure creatine does not lead to any improvement as this isolated compound cannot penetrate cerebral cells in CTD patients. Administration of creatine precursors has also failed, showing that this therapeutic approach, though efficient for other creatine deficiency disorders (AGAT and GAMT), is not suitable to treat CTD patients. Experimental creatine derivatives have been assessed as well, but they also failed in improving the CTD condition, mainly because of lack of stability and the toxicity of the tested molecules.

There is hence currently no treatment for CTD [7,8].

The patent application US 2015/0238453 proposes creatine derivatives with enhanced solubility in order to improve their bioavailability and their in vivo performance in particular to improve the CTD conditions [9]. Among the creatine derivatives disclosed in this application, there are N-acyl creatines and their aliphatic esters. One particular example thereof is one N-acyl creatine in which the acyl group replacing an active hydrogen in the amino group in creatine is DHA. Clearly, the DHA is covalently linked to the creatine or to the creatine aliphatic ester. In addition, the non-aqueous composition comprising the creatine derivatives as defined in [9] can be administrated orally, topically, transdermally or by intravenous route.

The present inventors previously reported that creatine fatty esters such as, for example, dodecyl creatine ester (DCE) might be a good therapeutic option for patients suffering from CrT deficiency. The proposed treatment has been already screened in vitro for Blood Brain Barrier (BBB) translocation, delivery in endothelial and astroglial cells, and conversion of creatine fatty and, in particular, DCE to Cr [10,11]. Preliminary behavioral analysis in CrT−/y mice revealed that DCE (0.02 mg/g body/weight/day for 5 days) significantly improves the performance of animals in the object recognition task after intracerebroventricular administration. These results thus support the value of the prodrug strategy for treating CTD, using creatine fatty esters with DCE being the most promising lead among them.

However, creatine fatty esters are degraded by plasma esterases in all biological fluids thus an efficient delivery system to target creatine fatty esters to the brain cells is needed to overcome CrT deficiency.

To solve this technical problem, the present inventors incorporated DCE in lipid nanocapsules (LNC) made of biocompatible material with polyethylene glycol present on their surface [12]. The inventors showed that these LNC loaded with DCE could cross in vitro BBB and entered brain endothelial cells. In human fibroblasts lacking CrT, all or part of the DCE was released from the LNC and biotransformed to creatine. Despite these promising results, the preparation of the LNC incorporating creatine fatty esters using a non ionic surfactant which is Transcutol® (from Gattefossé), needs three cycles of progressive heating and cooling between 60° C. and 90° C. before adding Transcutol® containing creatine fatty esters. Such a process with several steps at high temperatures attempts to the stability of this compound.

Clearly there is a need for a new pharmaceutical development comprising creatine fatty ester or a salt thereof made from safely excipients and easily to scale up for use in medicine and in particular dedicated to the treatment of CTD patients.

DISCUSSION OF THE INVENTION

The present invention improves the above-listed drawbacks and provides a solution to the aforementioned need. Indeed, the inventors have conceived a composition based on the use of creatine fatty ester such as dodecyl creatine ester, a glyceride-based oil and an omega-3 fatty ester such as 3 DocosaHexaenoic Acid (DHA) for nasal route in order to improve brain performance in creatine transporter knockout (CrT ko) mice.

This composition presents a specific characteristic in terms of solubility, stability and preservation of degradation by esterases. Indeed this composition makes possible to deliver creatine fatty ester or salt thereof by nasal administration and thus by-assing the BBB and preventing from a degradation by plasmatic enzymes of the creatine fatty ester or salt thereof. In addition, this composition is suitable for an industrial scale production.

This approach shall provide the significant increase in the creatine content in the different brain regions and thus to rescue the cognitive function in CTD patients.

In addition, the present invention is an attractive therapeutic strategy for the treatment of the brain diseases and disorders in which mitochondria dysfunctions have been documented. Indeed, the present invention is a creatine prodrug that aims at overcoming the poor pharmacokinetics properties of the drug itself. The creatine prodrug should overcome the drawback of the creatine regulation in mitochondria dysfunction-related diseases.

More particularly, the present invention concerns a composition comprising at least one creatine fatty ester or salt thereof, at least one omega 3 fatty acid or salt thereof and at least one glyceride for use in medicine, said composition being free of non ionic surfactants.

The composition implemented in the present invention comprises at least one creatine fatty ester or salt thereof. Advantageously, a creatine fatty ester is represented by the formula (I):

$$(NH_2)—C(NH)—N(CH_3)—CH_2—COOR \tag{I}$$

in which R represents an alkyl radical with 4 to 30 carbon atoms, an alkenyl radical with 4 to 30 carbon atoms or an aryl radical with 6 to 30 carbon atoms.

Regarding R, by «alkyl radical with 4 to 30 carbon atoms» is meant a linear, branched or cyclic (hetero)alkyl group, optionally substituted, with 4 to 30 carbon atoms, notably with 4 to 25 carbon atoms and in particular, with 4 to 20 carbon atoms, the heteroatom(s) of the heteroalkyl group being N, O, P or S.

Regarding R, by «alkenyl radical with 4 to 30 carbon atoms» is meant a linear, branched or cyclic (hetero)alkenyl group, optionally substituted, with 4 to 30 carbon atoms, notably with 4 to 25 carbon atoms and in particular, with 4 to 20 carbon atoms, the heteroatom(s) of the heteroalkenyl group being N, O, P or S.

Regarding R, by «aryl radical with 6 to 30 carbon atoms», is meant a mono- or poly-cyclic (hetero)aromatic group, optionally substituted, having from 6 to 30 carbon atoms, notably from 6 to 25 carbon atoms, in particular, from 6 to 20 carbon atoms, the heteroatom(s) of the heteroaromatic group being N, O, P or S.

Within the scope of the present invention, by «optionally substituted» is meant a radical which can be substituted with one or more groups selected from an alkyl group, an aryl group, an alkoxy group, a halogen, a hydroxy, a cyano, a trifluoromethyl or a nitro. For substitution groups, an «alkyl group» is a linear, branched or cyclic (hetero)alkyl group with 1 to 10 carbon atoms, the heteroatom(s) of the heteroalkyl group being N, O, P or S. For substitution groups, an «aryl group» is a mono- or poly-cyclic (hetero)aromatic group having from 6 to 15 carbon atoms, the heteroatom(s) of the heteroaromatic group being N, O, P or S. For substitution groups, an «alkoxy group» is an oxygen atom substituted by an alkyl group as above defined.

Within the scope of the present invention, by «halogen» is meant a fluorine, chlorine, bromine or iodine.

In a particular embodiment of the present invention, the radical R present in the creatine fatty ester of formula (I) is represented by the following formula (II):

$$—CH_2—R' \tag{II}$$

in which R' is chosen in the group consisting of an alkyl radical with 3 to 30 carbon atoms, an alkenyl radical with 3 to 30 carbon atoms and an aryl radical with 6 to 30 carbon atoms.

Regarding R', by «alkyl group with 3 to 30 carbon atoms» is meant a linear, branched or cyclic (hetero)alkyl group, optionally substituted, with 3 to 30 carbon atoms, notably with 3 to 25 carbon atoms and in particular, with 3 to 20 carbon atoms, the heteroatom(s) of the heteroalkyl group being N, O, P or S.

Regarding R', by «alkenyl group with 3 to 30 carbon atoms» is meant a linear, branched or cyclic (hetero)alkenyl group, optionally substituted, with 3 to 30 carbon atoms, notably with 3 to 25 carbon atoms and in particular, with 3 to 20 carbon atoms, the heteroatom(s) of the heteroalkenyl group being N, O, P or S.

In the composition implemented in the present invention, the creatine fatty ester can be present in the form of a salt of creatine fatty ester.

Within the scope of the present invention, «salt» refers to acid addition salts and base addition salts. Such salts can be formed by conventional means, for example by reaction of a form of free acid or a form of free base of a compound implemented in the invention with one or several equivalents of an appropriate acid or base, optionally in a solvent, or in a medium in which the salt is insoluble, then by extracting said solvent, or said medium, by using conventional techniques (for example in vacuum or by freeze drying). The salts can also be prepared by replacing a counter-ion of a compound implemented in the invention in the form of a salt with another counter-ion, for example by using an appropriate ion-exchange resin.

Especially in the purpose of being administered to a human or animal body, the salts of the compounds implemented in the invention are advantageously pharmaceutically acceptable salts.

In particular, when the compounds implemented in the invention are in the form of a salt, the latter being a salt of an alkali metal, in particular sodium or potassium salt, or salt of alkaline earth metal, in particular magnesium or calcium, or even a salt with an organic amide, more particularly with an amino acid such as arginine or lysine.

When the compounds implemented in the invention which have an amine function are in the form of a salt of this amine, the salt is a salt of inorganic acid such as, for example, hydrochloric acid, sulfuric acid, or hydrobromic acid, or in the form of an organic salt, such as, for example, acetic acid, formic acid, triflic acid, tartatic acid, oxalic acid, citric acid, trifluoroacetic acid or methanesulfonic acid.

Advantageously, the creatine fatty esters and salts thereof implemented in the present invention can present one or more radioisotope(s), in particular chosen from iodine-123, iodine-125, iodine-126, iodine-133, iodine-131, iodine-124, indium-111, indium-113m, bromine-77, bromine-76, gallium-67, gallium-68, ruthenium-95, ruthenium-97, technetium-99m, fluorine-19, fluorine-18, carbon-13, carbon-11, nitrogen-15, nitrogen-13, oxygen-17, oxygen-15, oxygen-14, scandium-47, tellurium-122m, thulium-165, yttrium-199, copper-64, copper-62, gadolidium-68 and rubidium-82.

In the present invention, the composition implemented can contain only one creatine fatty ester or only one salt thereof. Alternatively, the composition can contain at least two different creatine fatty esters, at least two different creatine fatty ester salts or a mixture of at least one creatine fatty ester and at least one creatine fatty ester salt.

As particular examples of creatine fatty esters and salts thereof implemented in the present invention, one can cite DCE or a salt thereof such as, for example, hydrochloride salt of DCE.

In the composition implemented in the invention, the at least one creatine fatty ester or salt thereof, i.e. the creatine fatty ester(s) and/or salt(s) thereof, is present in an amount of 0.01% to 6% by weight and in particular of 0.02% to 5.5% by weight based on the total weight of the composition.

The composition implemented in the present invention comprises, in addition to creatine fatty ester(s) and/or salt(s) thereof, at least one omega-3 fatty ester or a salt thereof. It should be noted that, in the composition implemented in the present invention, there is no covalent link between an omega-3 fatty ester or a salt thereof and a creatine fatty ester or a salt thereof.

An omega-3 fatty ester is an unsaturated fatty acid that presents a terminal moiety CH$_3$—CH$_2$—CH=CH— and that can be represented by the following formula (III):

$$CH_3—CH_2—CH=CH—R_1—C(=O)—OR_2 \qquad (III)$$

in which $R_1$ represents an alkylene chain or an alkenylene chain and in which $R_2$ represents H or an alkyl group.

Regarding $R_1$, «alkylene chain» is taken to mean a linear, branched or cyclic alkylene chain, optionally substituted, comprising from 1 to 40 carbon atoms, particularly from 2 to 30 carbon atoms and which can optionally comprise at least one heteroatom. By way of examples of alkylene chains that may be used, methylene, ethylene, n-propylene, isopropylene, butylene, isobutylene, sec-butylene, tert-butylene, pentylene, isopentylene, hexylene, cyclopentylene, cyclohexylene, —(CH$_2$)$_n$—O—(CH$_2$)$_m$—, —(CH$_2$)$_n$—S—(CH$_2$)$_m$—, —(CH$_2$)$_n$—S—S—(CH$_2$)$_m$—, —(CH$_2$)$_n$—C(O)O—(CH$_2$)$_m$— groups may be cited with n and m, identical or different, representing a whole number comprised between 0 and 20.

Regarding $R_1$, «alkenylene chain» is taken to mean a linear, branched or cyclic alkenylene chain, optionally substituted, comprising from 3 to 40 carbon atoms and particularly from 4 to 30 carbon atoms and which can optionally comprise at least one heteroatom. By definition, an alkenylene chain comprises at least one carbon carbon double bond. Typically, regarding $R_9$, the alkenylene chain can comprise 1, 2, 3 or 4 carbon carbon double bond(s). As examples of alkenylene chains being able to be used, butenylene, isobutenylene, sec-butenylene, tert-butenylene, pentenylene, isopentenylene, cyclopentenylene or cyclohexenylene groups may be cited.

Regarding $R_2$, «alkyl group» is taken to mean a linear, branched or cyclic alkyl group, optionally substituted, comprising from 1 to 40 carbon atoms, particularly from 2 to 30 carbon atoms and which can optionally comprise at least one heteroatom, the heteroatom(s) of the heteroalkyl group being N, O, P or S.

In the present invention, the composition implemented can contain only one omega-3 fatty ester or only one salt thereof. Alternatively, the composition can contain at least two different omega-3 fatty esters, at least two different omega-3 fatty ester salts or a mixture of at least one omega-3 fatty ester and at least one omega-3 fatty ester salt.

As particular examples of omega-3 fatty esters or salts thereof implemented in the present invention, one can cite linoleic acid, octadecatetraenoic acid, eicosapentaenoic acid, docosahexaenoic acid, docosapentaenoic acid and salt thereof. More particularly, in the composition implemented in the invention, the omega-3 fatty ester implemented is docosahexaenoic acid (DHA) or a salt thereof.

What has been previously explained for a salt of creatine fatty ester also applies to a salt of an omega-3 fatty ester mutatis mutandis. Additional information on salt of an omega-3 fatty ester can also be found in paragraph [0086] of [4].

In the composition implemented in the invention, the at least one omega-3 fatty ester or salt thereof, i.e. the omega-3 fatty ester(s) and/or salt(s) thereof, is present in an amount of 15% to 35% by weight and in particular from 20% to 30% by weight based on the total weight of the composition.

The composition implemented in the present invention also comprises, in addition to creatine fatty ester(s) and/or salt(s) thereof and omega-3 fatty ester(s) and/or salt(s) thereof as previously defined, at least one glyceride.

The term «glyceride» refers to an ester of glycerol (1,2,3-propanetriol) with acyl radicals of fatty acids. Within the present invention, the terms and expression «glyceride», «acylglycerol», «glyceride fatty ester» and «glycerolipid» are equivalent and can be used interchangeably.

In a glyceride, if only one position of the glycerol molecule is esterified with a fatty acid, a «monoglyceride» is produced; if two positions are esterified, a «diglyceride» is produced; and if all three positions of the glycerol are esterified with fatty acids, a «triglyceride» is produced. A glyceride is «simple» if all esterified positions contain the same fatty acid; whereas a glyceride is «mixed» if the esterified positions are substituted with different fatty acids. A glyceride is «complex» if it contains a combination of simple and mixed glycerides.

In the composition implemented in the present invention, the at least one glyceride is a single glyceride such as a single monoglyceride, a single diglyceride or a single triglyceride. Alternatively, the at least one glyceride is a mixture containing at least two different glycerides such as a mixture containing at least two different monoglycerides, a mixture containing at least two different diglycerides, a mixture containing at least two different triglycerides, a mixture containing at least one monoglyceride and at least one diglyceride, a mixture containing at least one monoglyceride and at least one triglyceride and a mixture containing at least one diglyceride and at least one triglyceride. In a particular embodiment, the at least one glyceride is a mixture containing at least one monoglyceride, at least one diglyceride and at least one triglyceride.

In the glyceride(s) implemented in the composition according to the present invention, the acyl radical(s) comprise(s) from 4 to 36 carbon atoms, advantageously from 5 to 30 carbon atoms and, in particular, from 6 to 24 carbon atoms. This/these acyl radical(s) can be saturated or unsaturated. In the latter case, the acyl radical presents at least one carbon carbon double bond and advantageously 1, 2, 3 or 4 carbon carbon double bonds.

As examples of acyl radicals which can be present in the glyceride(s) of the composition according to the invention, one can cite the acyl groups of the following fatty acids: caproic acid, caprylic acid, capric acid, undecylic acid, lauric acid, myristic acid, tridecylic acid, palmitic acid, margaric acid, stearic acid, nonadecylic acid, arachidic acid, heneicosylic acid, behenic acid, lignoceric acid, cerotic acid, palmitoleic acid, myristoleic acid, linoleic acid, sapienic acid, oleic acid, gadoleic acid, elaidic acid, vaccenic acid, linoelaidic acid, a-linolenic acid, arachidonic acid, eicosapentaenoic acid, erucic acid and docosahexaenoic acid.

The glyceride(s) present in the composition implemented in the present invention can be natural or synthetic. In particular, this/these glyceride(s) are present in vegetable and animal fats and oils and, if necessary, can be extracted therefrom by conventional methods. When the at least one glyceride is a mixture of different glycerides, the latter can be prepared by admixing the different glycerides in appropriate relative proportion. Alternatively this mixture can comprise transesterification products of vegetable oils with glycerol. The one skilled in the art knows methods to perform this transesterification. Additional information on these methods can be found in the patent application EP 0 589 843 [13].

As examples of particular vegetable oils usable as source of glyceride(s) and/or for transesterification, one can cite argan oil, almond oil, avocado oil, beech oil, cashew oil, castor oil, coconut oil, colza oil, corn oil, cottonseed oil, grapefruit seed oil, grape seed oil, hazelnut oil, hemp oil, lemon oil, macadamia oil, mustard oil, olive oil, orange oil, palm oil, peanut oil, pecan oil, pine nut oil, pistachio oil, poppyseed oil, rapeseed oil, rice bran oil, safflower oil, sesame oil, soybean oil, sunflower oil, walnut oil and wheat germ oil.

As particular examples of glyceride or mixture of glycerides which can be used in the composition implemented in the present invention, one can cite:
- a triglyceride obtained by esterification of caprylic (octanoic) acid and glycerol, such a triglyceride is sold by Abitec Corporation under the trademark CAPTEX 8000;
- a mixture of triglycerides, obtained by esterification of glycerol with caprylic (octanoic) and capric (decanoic) acids, such a mixture is sold by Cremer under the trademarks Mygliol 810 and Mygliol 812; it is also sold by Gattefossé under the trademark Labrafac WL1349;
- a mixture of monoglycerides, obtained by esterification of glycerol with caprylic (octanoic) and capric (decanoic) acids, such a mixture is sold by Abitec Corporation under the trademark CAPMUL MCM EP;
- a mixture of mono-, di- and triglycerides of linoleic ($C_{18:2}$) and oleic ($C_{18:1}$) acids, the diester fraction being preferably predominant, such a mixture is sold by Gattefossé under the trademark MAISINE CC; and
- a mixture of mono-, di- and triglycerides of oleic ($C_{18:1}$) acid, the monoester fraction being preferably predominant, such a mixture is sold by Gattefossé under the trademark Peceol.

In a particular embodiment, the at least one glyceride is a mixture of mono-, di- and triglycerides of linoleic ($C_{18:2}$) and oleic ($C_{18:1}$) acids, the diester fraction being preferably predominant, such a mixture is sold by Gattefossé under the trademark MAISINE CC.

In the composition implemented in the invention, the at least one glyceride, i.e. the glyceride(s), is present in an amount of 60% to 85% by weight and in particular of 70% to 80% by weight based on the total weight of the composition.

The composition implemented in the present invention does not comprise any non-ionic surfactant.

As a reminder, non-ionic (or neutral) surfactants are compounds wherein the surfactant properties, particularly the hydrophilic properties, are provided by non-charged functional groups such as an alcohol, an ether, an ester or an amide, and may contain heteroatoms such as nitrogen or oxygen. Due to the low hydrophilic contribution of these functions, the non-ionic surfactants are generally polyfunctional. The non-ionic surfactant(s) can be non-ionic hydrophilic surfactant(s), non-ionic lipophilic surfactant(s) or mixtures thereof.

As examples of non ionic surfactants not present in the composition implemented in the present invention, one can cite non-ionic surfactants selected from the group consisting of alkyl alkoxylates; fatty alcohol alkoxylates; fatty amine alkoxylates; fatty acid alkoxylates; oxo alcohol alkoxylates; alkylphenol alkoxylates; alkyl ethoxylates; fatty acid ethoxylates; fatty amine ethoxylates; fatty acid ethoxylates; oxo alcohol ethoxylates; alkylphenol ethoxylates such as, for example, octylphenol and nonylphenol ethoxylates; alcohols, α-diols, polyethoxylated and poly-propoxylated alkylphenols having a fatty chain including, for example, 8 to 18 carbon atoms, the number of ethylene oxide or propylene oxide groups optionally being particularly from 2 to 50; polyoxylglycerides; polyethylene oxides; polypropylene oxides; polyethylene and polypropylene oxide complex polymers; ethylene and propylene oxide copolymers; polyethylene and polypropylene oxide block copolymers such as, for example, POE-POP-POE triblock copolymers; ethylene and propylene oxide condensates on fatty alcohols; polyethoxylated oils; polyethoxylated alcohols; polyethoxylated fatty amides having, preferably, 2 to 30 moles of ethylene oxide; polyethoxylated ethers having, preferably, 2 to 30 moles of ethylene oxide; monoesters (monolaurate, monomyristate, monostearate, monopalmitate, monooleate, etc.) and polyesters of fatty acids and glycerol; polyglycerolated fatty amides comprising on average from 1 to 5 and, more especially, from 1.5 to 4 glycerol groups; oxyethylenated sorbitan fatty acid esters including 2 to 30 moles of ethylene oxide; monoesters (monolaurate, monomyristate, monostearate, monopalmitate, monooleate, etc.) and polyesters of fatty acids and sorbitan, polyoxyethylene sorbitan monoesters; sucrose esters of fatty acids; propylene glycol esters of fatty acids; polyethylene glycol esters of fatty acids; alkyl polyglucosides; N-alkyl glucamine derivatives and amine oxides such as alkyl($C_{10}$-$C_{14}$) amine oxides or N-acylaminopropylmorpholine oxides; polyols (surfactants derived from sugars) in particular glucose alkylates such as for example glucose hexanate; surfactants derived from glucoside (sorbitol laurate) or polyols such as glycerolated alcohol ethers; alkanolamides and mixtures thereof.

As particular examples of non ionic surfactants not present in the composition implemented in the present invention, one can cite selected from the group consisting of polyoxyethylene sorbitan monoesters such as, for example, polyoxyethylene (20) sorbitan monooleate (also known as Polysorbate 80 or Tween 80); polyethoxylated oils such as, for example, the polyethoxylated castor oil (sold by BASF under the trademark Kolliphor EL, formerly known as Cremophor EL); polyethylene oxides such as, for example, PEG 400; propylene glycol esters of fatty acids such as, for example, propylene glycol monocaprylate (sold by Gattefossé under the trademark Capryol 90), propylene glycol dicaprylate/caprate (sold by Cremer under the trademark Miglyol 840 or sold by Abitec Corporation under the trademark Captex 200) and propylene glycol monolaurate (sold by Gattefossé under the trademark Lauroglycol FCC); polyoxylglycerides such as, for example, caprylocaproyl polyoxy-8 glycerides (sold by Gattefossé under the trademark Labrasol ALF) or oleoyl polyoxyl-6 glyceride (sold by Gattefossé under the trademark Labrafil M 1944) and polyethoxylated alcohols such as, example, 2(2-ethoxyethoxy) ethanol also known as diethylene-glycol-monoethyl ether (sold by Gattefossé under the trademark Transcutol HP).

In a particular embodiment, the composition implemented in the present invention does not comprise citicoline.

The composition implemented in the present invention can comprise at least one additional element such as, for example, water, an alcohol substance of low molecular weight such as ethanol, glycerol, propanediol or 1,3-butanediol or a thickener.

Alternatively, the composition implemented in the present invention consists of at least one creatine fatty ester or salt thereof, at least one omega 3 fatty acid or salt thereof and at least one glyceride. As particular examples of such a composition, one can cite:

a composition consisting of 2% by weight of at least one creatine fatty ester or salt thereof, 24.5% by weight at least one omega 3 fatty acid or salt thereof and 73.5% by weight of at least one glyceride, based on the total weight of the composition and a composition consisting of 4% by weight of at least one creatine fatty ester or salt thereof, 24% by weight at least one omega 3 fatty acid or salt thereof and 72% by weight of at least one glyceride, based on the total weight of the composition.

Depending on the constituents present in the composition implemented in the present invention, this composition may have different forms such as, for example, an oil or oily phase, micelles, a suspension, an emulsion, a macro-emulsion, a nano-emulsion or a micro-emulsion.

The composition implemented in the present invention can be prepared by a method comprising a step consisting in mixing at least one creatine fatty ester or salt thereof as previously defined, at least one omega 3 fatty acid or salt thereof as previously defined and at least one glyceride as previously defined.

Before said mixing step, the method may comprise an additional step consisting in preparing the creatine fatty ester(s) and/or salt(s) thereof. The one skilled in the art knows different methods for preparing a creatine fatty ester or a salt thereof.

Some methods involve Brönsted acids-catalyzed reaction of creatine with alcohols. These methods are well adapted to alcohols of low molecular weight such as EtOH, nPrOH, and nBuOH but yield are dramatically reduced in case of fatty, long chain alcohols. Then the method disclosed in [10] and implemented in [11,12] can also be used to prepare creatine fatty esters.

For said mixing step, the different elements can be added in a recipient in any order and even as mixture in order to prepare the composition. As a consequence, before mixing, the method can comprise a stage consisting in:

adding at least one omega 3 fatty acid or salt thereof in the recipient, then adding at least one glyceride and finally adding at least one creatine fatty ester or salt thereof;

(ii) adding at least one omega 3 fatty acid or salt thereof in the recipient, then adding at least one creatine fatty ester or salt thereof and finally adding at least one glyceride;

(iii) adding at least one glyceride in the recipient, then adding at least one omega 3 fatty acid or salt thereof and finally adding at least one creatine fatty ester or salt thereof;

(iv) adding at least one glyceride in the recipient, then adding at least one creatine fatty ester or salt thereof and finally adding at least one omega 3 fatty acid or salt thereof;

(v) adding at least one creatine fatty ester or salt thereof in the recipient, then adding at least one omega 3 fatty acid or salt thereof and finally adding at least one glyceride;

(vi) adding at least one creatine fatty ester or salt thereof in the recipient, then adding at least one glyceride and finally adding at least one omega 3 fatty acid or salt thereof;

(vii) adding at least one omega 3 fatty acid or salt thereof in the recipient containing a previously prepared mixture comprising at least one creatine fatty ester or salt thereof and at least one glyceride;

(viii) adding at least one glyceride in the recipient containing a previously prepared mixture comprising at least one creatine fatty ester or salt thereof and at least one omega 3 fatty acid or salt thereof; or (ix) adding at least one creatine fatty ester or salt thereof in the recipient containing a previously prepared mixture comprising at least one glyceride and at least one omega 3 fatty acid or salt thereof.

Advantageously, the stage (vi) as defined above is performed during method for preparing the composition implemented in the present invention.

When the composition implemented in the invention comprises several creatine fatty esters or salts thereof, these compounds can be added at a single time or added one after the other or in groups in any of the stages (i) to (ix) as previously defined. A mixture of these compounds is advantageously added in any of the stages (i) to (ix) as previously defined. The same applies mutatis mutandis when the composition implemented in the invention comprises several omega 3 fatty acids or salts thereof and/or several glycerides.

Mixing is conducted under agitation by simple mechanical means using a magnetic bar, a magnetic stirrer, an ultrasound bath, a vortex, a thermomixer or homogenizer. In a particular embodiment, the mixing in the step previously defined consists in a vortexing step followed by a shaking step performed in a thermomixer. The vortexing step may be carried out at a temperature of between 10° C. and 40° C., advantageously between 15° C. and 30° C. and more particularly at room temperature (i.e. 23° C.±5° C.) for a time of between 1 min and 15 min, in particular between 2 min and 10 min, more particularly for about 5 min (i.e. 5 min±1 min). The shaking step may be carried out at a speed of between 500 and 2000 g and advantageously at a speed of about 1000 g (i.e. 1000 g±200 g), at a temperature of between 20° C. and 50° C., advantageously between 25° C. and 40° C. and more particularly at a temperature of about 30° C. (i.e. 30° C.±2° C.) for a time of between 12 h and 4 d, in particular between 24 h and 3 d, more particularly for about 48 h (i.e. 48 h±4 h).

Before using the composition thus prepared, the method may comprise an additional step consisting in eliminating any undissolved creatine fatty ester or salt thereof from composition obtained after the mixing step. Advantageously, this additional step can comprise a centrifugation step followed by a filtration step. The centrifugation step may be carried out at a speed of between 10000 g and 30000 g and advantageously at a speed of about 20000 g (i.e. 20000 g±5000 g), at a temperature of between 4° C. and 40° C., advantageously between 10° C. and 30° C. and more particularly at room temperature for a time of between 5 min and 30 min and, in particular for about 15 min (i.e. 15 min±5 min) or for about 10 min (i.e. 10 min±5 min). The supernatant obtained after said centrifugation step is filtered during said filtration step that may be carried out through a 0.22 μm filter. When the method comprises a centrifugation step followed by a filtration step, the composition for use in medicine is the filtrate obtained after the filtration step.

As already defined, the present invention concerns a composition as previously defined for use in medicine.

Indeed, thanks to the in vivo investigations performed by the inventors, it is clear that the composition implemented the invention can convey creatine fatty ester or salt thereof in the brain, in particular through peripheral or nasal administration, in order to restore creatine pool, since creatine fatty ester or salt thereof are degradable by plasma esterases in all biological fluids. The inventors have tested the efficacy of this composition in improving the brain performance of creatine transporter knock-out (CrT ko) mice and in particular their cognitive functions. It should be noted that this composition protects the creatine fatty ester or salt thereof it contains from degradation while administration to a subject.

Also disclosed is the use of such a composition able to by-pass the BBB in vivo without the involvement of Solute Large Carrier Transporter (SLC6A8) notably thanks to a nasal administration. So that creatine normally excluded by the BBB in patients with creatine transporter deficiency may be produced after cleavage of creatine fatty esters within the brain endothelial cells and released in the brain parenchyma.

Thus, this composition is used in medicine and notably in therapeutic medicine, in medical diagnosis and in medical imaging such as by Positron Emission Tomography (PET). Indeed, the fact that the creatine part and/or the fatty ester part of the creatine fatty ester or of the salt thereof can present radioisotope(s) as previously disclosed can be useful in diagnosis and in imaging.

The present invention concerns a composition as previously defined for use in the treatment or the prevention of at least one disease, disorder or condition selected in the group consisting of a neuromuscular disorder such as, for example, Duchene metabolic disorder; hypoxia; an ischemic brain disease such as stroke or perinatal brain injury; an heart disease; a muscular dystrophy; a skin disorder; a neurodegenerative disease such as, for example, amyolateral sclerosis (also known as amyotrophic lateral sclerosis), Parkinson's disease and Huntington's disease; leukodystrophy such as, for example, adrenoleukodystrophy, metachromatic leukodystrophy and Alexander disease; a psychiatric disorder such as, for example, bipolar syndrome or autism; aging; and inflammation. In particular, the composition implemented in the present invention can be used for the treatment or the prevention of at least one disease, disorder or condition selected in the group consisting of a neuromuscular disorder such as, for example, Duchene metabolic disorder; hypoxia; a neurodegenerative disease such as, for example, amyolateral sclerosis (or amyotrophic lateral sclerosis), Parkinson's disease and Huntington's disease; and an ischemic brain disease such as stroke or perinatal brain injury.

In Duchene Metabolic Disorder (DMD), a loss of independent ambulation occurs between the ages of 6 and 13 years, the average being 9.5 years in non-steroid treated patients. Once ambulation is lost, joint contractures and scoliosis develop rapidly. Cardiomyopathy and respiratory failure are the cause of death in young adulthood. Cognitive dysfunction affects around 30% of DMD patients with a smaller total brain volume, smaller grey matter volume, lower white matter fractional anisotropy and higher white matter radial diffusivity. A clinical trail was performed on 18 patients vs placebo (5 g of creatine/day for 8 weeks). The results indicated that creatine was well tolerated and oral creatine significantly improved the muscle Phosphocreatine/Inorganic Phosphate ratio and preserved the muscle strength in short term [14].

In stroke, the interest of creatine in post-traumatic cerebral injuries is consistent with creatine cellular role, supplementation reduced neuronal damage, protected against the effects of cellular energy crisis and improved cognitive and somatic symptoms [15,16].

In perinatal brain injury, during the primary phase following asphyxia, neuronal energy failure occurs through a rapid decrease of high energy phosphates: phosphocreatine (P—Cr). Bringing and increasing P-cr in the different brain regions through the nasal administration of creatine ester derivative or salt thereof will be effective in the treatment of perinatal brain injury. This assertion is supported by the facts that in perinatal brain injury, creatine supplementation reduces ATP depletion after schemic injury [17] thereby protecting neurons from oxygen glucose deprivation mediated apoptosis and necrosis [18].

The deleterious mechanisms due to a defect in glutamate reuptake also appear to be involved in amyotrophic lateral sclerosis (ALS), which leads to degeneration of motor neurons in the motor cortex and spinal cord. The most widespread form of the disease is a familial form expressing various mutations in the gene coding for superoxide dismutase (SOD), a metallo-proteinase with antioxidant properties. This leads to mitochondrial energy defects. The mutated SOD is no longer able to exert its anti-oxidant activity and there is not only an increase in oxygen radical species but also a decreased enzymatic activity of the respiratory chain complexes. This contributes to morphological changes in the mitochondria resulting in particular from the decrease in mitochondrial membrane potentials, swelling of the mitochondria and the formation of a vacuole. The consequence is a decrease in ATP [19].

Parkinson's disease (PD) is a degenerative neurological disease that is manifested by tremor, rigidity, bradykinesia and postural instability. Although PD is characterized neuropathologically by alpha-synuclein-immunopositive Lewy bodies in the substantia nigra and other brainstem structures, there is in increasing recognition that PD is a diffuse brain disease involving both cortical and subcortical structure. Dysfunction of mitochondrial oxidative metabolism has been implicated in the pathogenesis of PD though a variety of mechanisms including reduced ATP production and generation of free radicals [20]. Diminished activity in complex I of the mitochondrial electron transport system (ETS) in post-mortem brain tissue has been reported in cortex and substantia nigra. Therefore, the creatine properties could be an attractive strategy to impair mitochondria dysfunction [21]. Since the dopaminergic and adrenergic neurons don't possess the creatine transporter, creatine supplementation o will not be efficient to overcome mitochondria dysfunction associated with PD. Bringing DCE through its nasal administration will overcome this limitation through the distribution of creatine in neurons despite the lack of creatine transporter in the different brain regions as the striatum.

Huntington's disease (HD) is a progressive autosomal dominant inherited neurological disease that leads to motor and cognitive disorders. It is due to nucleotide repeats (CAG) in the gene coding for huntingtin that leads to abnormal repetition of polyglutamine in the protein sequence. In a pathological context, the mutated protein leads to cell death of striatal neurons. Alterations in cellular energy metabolism are responsible for the expansion of the disease. The mutated protein decreases mitochondrial function, ATP concentration and an increase in oxygen radical species [22]. In particular, patients have decreased muscle phosphocreatine levels. A double-blind, placebo-controlled clinical study of 64 patients receiving 8 g/day creatine supplementation for 16 weeks showed a marked decrease in serum 8-hydroxy-2'-deoxyguanosine, a marker of oxidative DNA damage [23], suggesting the potential role of creatine supplementation. Therefore, bringing efficiently creatine through nasal administration of DCE could be a promising therapy for the treatment of Huntington's disease.

Psychiatric disorders such as bipolar syndrome, are associated with dysfunction of creatine mitochondria and more particularly, by a decrease of mitochondria kinase activity and/or of P—Cr [24-26].

Concerning aging, it was shown that creatine improves health and longevity in mice [28].

The present invention also concerns a composition as previously defined for use in the brain creatine transporter deficiency disease.

In other words, the present invention concerns a method for treating or preventing at least one disease, disorder or condition selected in the group consisting of a neuromuscular disorder such as, for example, Duchene metabolic disorder; hypoxia; an ischemic brain disease such as stroke or perinatal brain injury; an heart disease; a muscular dystrophy; a skin disorder; a neurodegenerative disease such as, for example, amyolateral sclerosis (also known as amyotrophic lateral sclerosis), Parkinson's disease and Huntington's disease; leukodystrophy such as, for example, adrenoleukodystrophy, metachromatic leukodystrophy and Alexander disease; a psychiatric disorder such as, for example, bipolar syndrome or autism; aging; and inflammation, consisting in administering to a subject in need, a therapeutic amount of a composition as previously defined. More particularly, the present invention concerns a method for treating or preventing at least one disease, disorder or condition selected in the group consisting of a neuromuscular disorder such as, for example, Duchene metabolic disorder; hypoxia; a neurodegenerative disease such as, for example, amyolateral sclerosis (or amyotrophic lateral sclerosis), Parkinson's disease and Huntington's disease; and an ischemic brain disease such as stroke or perinatal brain injury, consisting in administering to a subject in need, a therapeutic amount of a composition as previously defined.

The present invention also concerns a method for treating the brain creatine transporter deficiency disease, consisting in administering to a subject in need, a therapeutical amount of a composition as previously defined.

Additional information on such treatment methods can be found in [10] and in the bibliography cited therein, in particular, the documents referenced [1-4] in [10].

The composition implemented in the invention can be administered orally, nasally, parenterally (intravenous, intramuscular, or subcutaneous), topically, transdermally, intravaginally, intravesically, intracistemally, or rectally. Nasal administration is advantageous for any disease, disorder or condition affecting brain performance.

Other characteristics and advantages of the present invention will additionally be apparent to the one skilled in the art on reading the examples below, which are given as an illustration and not a limitation, with reference to the attached FIGURES.

SHORT DESCRIPTION OF THE DRAWINGS

The single FIGURE presents creatine content in different brain regions from $Slc6a8^{+/y}$ (control) and $Slc6a8^{-/y}$ mice after nasal administration of a composition implemented in the present invention (DCE-ME) or of the vehicle measured by liquid chromatography coupled to mass spectroscopy (LC/MS-MS). Data are mean±SEM. Mann-Whitney test *$P<0.05$.

DETAILED DISCUSSION OF PARTICULAR EMBODIMENTS

Synthesis of Hydrochloride Salt of Creatine Dodecyl Ester ($DCE_{HCl}$).

DCE was prepared according to the method described in [10] and implemented in [11,12]. The chlorhydrate was obtained by dissolution in excess HCl 0.01 N and evaporation to dryness to give $DCE_{HCl}$. The latter can be stored at 4° C. before use.

II. $DCE_{HCl}$ Composition Implemented in the Present Invention.

10 mg of $DCE_{HCl}$ were added with 0.375 g of Maisine® CC (Gattefossé) previously stored at room temperature. 0.125 g of DHA (Sigma-Aldrich) previously stored at −20° C. is added. The mixture was vortexed for 5 min and shaken in a thermomixer (1000 g at 30° C.) for 48 h. Then, a centrifugation process (20000 g—10 min at room temperature) was applied and the supernatant was filtered through a 0.22 μm filter, placed in another tube and storage at room temperature prior to use.

III. In Vivo Test of Nasal Administration.

The nasal route was adopted to exploit first its avoidance of the hepatic first-pass metabolism to increase the absolute bioavailability, and second the direct nose-to-brain pathway to enhance the brain drug delivery. The aim of this test was to evaluate the non-toxicity of the formulations implemented in the present invention and the ability of DCE to be translocated to the brain, to turn into creatine and to overcome CrT deficiency.

For this purpose, $Slc6a8^{-/y}$ mice i.e. creatine transporter knock-out mice were generated and genotyped in-house according to published study [28]. Male mice of 18-25 weeks old were used due to the X-linked nature of CTD. Mice were housed under standard experimental conditions: at room temperature; light/dark cycle (14 h light/10 h dark); water and food ad libitum, and kept in social groups of 4 mice per cage. The $Slc6a8^{-/y}$ mice were divided into 2 groups comprising 4-7 mice each, one group received the vehicle i.e. Maisine® CC+DHA (Vehicle) and the other one was treated with the composition prepared at point II (DCE-ME). Wild-type Slc6a8+/y mice were used as control.

The dose was given as nasal drops using a micropipette, divided equally into two nostrils (24 μl final volume/day of DCE-ME or of vehicle) for 5 consecutive days. Every day the animals were examined for any abnormal behavior, mortality and morbidity. At the end of the treatment, mice were sacrificed by cervical dislocation. Samples (cortex, hippocampus, striatum and cerebellum) were weighed and collected in tubes and storage at −80° C. prior to analysis. For LC/MS-MS quantifications the previously developed technique for Creatine brain analysis [11] was adapted.

No mortality was observed in any of the groups during the 5-day treatment period. Macroscopic examination of the brain sections exposed to the formulations did not show any change in the morphology or tissue microstructure as compared to normal control group mouse. No visible sign of inflammation or necrosis revealed the safety of the developed formulations.

Figure 1:
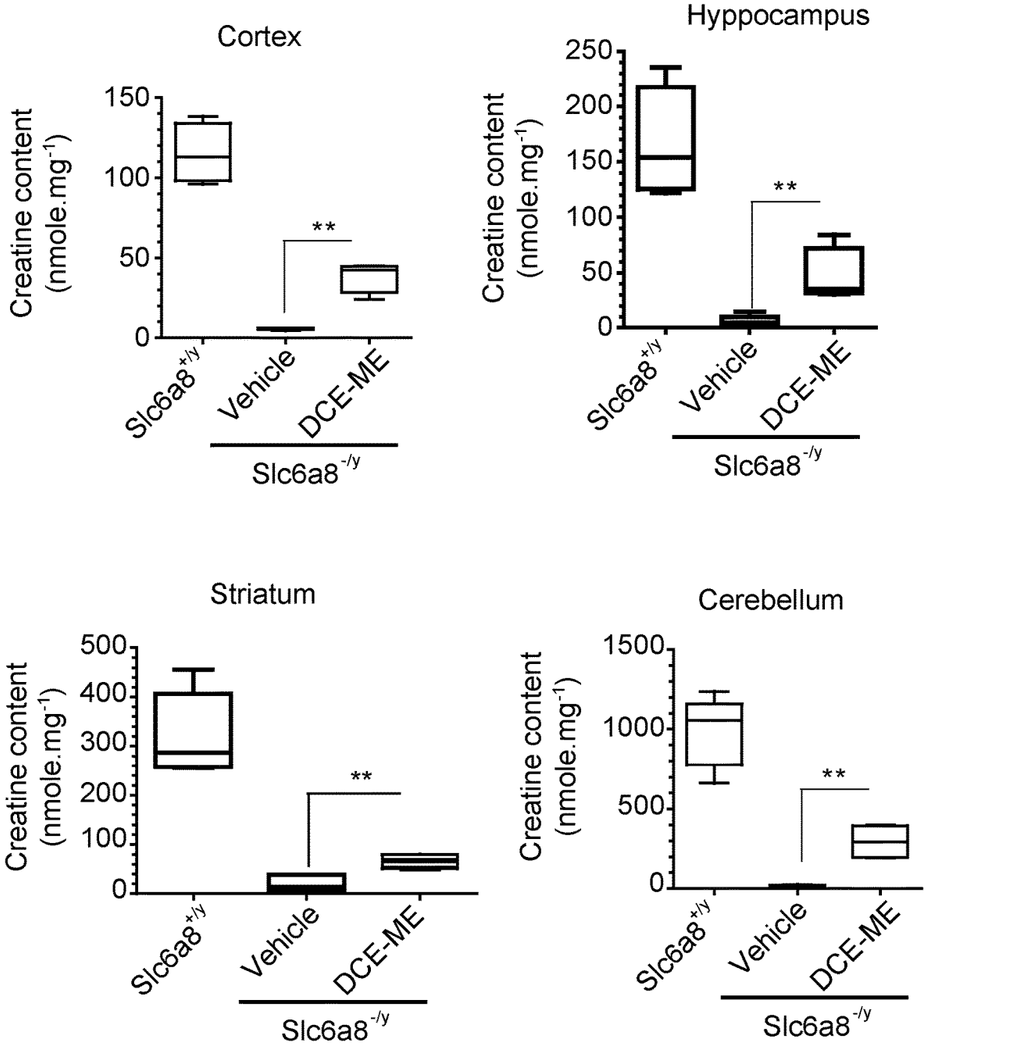

The single FIGURE shows the mean Creatine concentration per mg of protein in cortex, hippocampus, striatum and cerebellum tissues. Following nasal administration DCE-treated $Slc6a8^{-/y}$ mice (5 days, 24 μl/day) showed a significant increase in Cr brain content in striatum, cortex, hippocampus and cerebellum tissues compared with vehicle-treated $Slc6a8^{-/y}$ mice ($P<0.05$) even if there is some overlap in the lower quartile of the DCE-treated $Slc6a8^{-/y}$ vs the upper quartile of the vehicle-treated $Slc6a8^{-/y}$ mice. The overall effect was that there was an increase in mean Cr levels. The results of the experiment show no toxic effect of DCE, suggesting the safety of the composition implemented in to the present invention.

IV. Comparative Study of the Composition According to the Invention Versus Creatine Derivative or Salt Thereof.

First of all, in aqueous media, creatine ester is degraded to creatine and, as already explained, creatine does not lead to any improvement in CTD patients. Solubilisation of creatine ester or salt thereof can only be achieved by using strong acids.

An acid composition can be administrated neither intravenously, nor nasally. Indeed, for a good tolerance during these administrations, the compositions must present a pH ranging from 4.5 to 6.5. Such a pH respects the nasal mucosal pH.

Thus, it is impossible to have comparative data between the composition according to the present invention and the creatine ester or salt thereof, since the solubilisation of the creatine ester or salt thereof is performed at pH incompatible with an administration and in particular a nasal administration in humans and animals.

REFERENCES

[1] International application WO 02/22135 in the name of Board of Regents of the University of Nebraska, published on Mar. 21, 2002.

[2] Patent application US 2002/0049253 in the name of Kaddurah-Daouk, published on Apr. 25, 2002.

[3] Patent application US 2003/0212130 in the name of Miller et al, published on Nov. 13, 2003.

[4] International application WO 2015/120299 in the name of University of Utah Research Foundation, published on Aug. 13, 2015.

[5] Stöckler et al, 2007, "Cerebral creatine deficiency syndromes. Clinical aspects, treatment and pathophysiology", Subcell. Biochem., vol. 46, pages 149-166.

[6] Green D R, Galluzzi L, Kroemer G. Mitochondria and the autophagy-inflammation-cell death axis in organismal aging. Science. 2011; 333(6046):1109-1112]

[7] van de Kamp et al, 2014, "X-linked creatine transporter deficiency: clinical aspects and pathophysiology", J Inherit Metab Dis., vol. 37, pages 715-733.

[8] Kurosawa et al, 2012, "Cyclocreatine treatment improves cognition in mice with creatine transporter deficiency", J. Clin. Invest., vol. 122, pages 2837-2846.

[9] Patent application US 2015/0238453 in the name of 4141 HOLDINGS, LLC, published on Aug. 27, 2015.

[10] Patent application EP 2 692 719 in the name of Commissariat à l'Energie Atomique et aux Energies Alternatives, published on Feb. 5, 2014.

[11] Trotier-Faurion et al, 2013, "Synthesis and biological evaluation of new creatine fatty esters revealed dodecyl creatine ester as a promising drug candidates for the treatment of the creatine transporter deficiency", J. Med. Chem., vol. 56, pages 5173-5181.

[12] Trotier-Faurion et al, 2013, "Dodecyl creatine ester and lipid nanocapsule: a double strategy for the treatment of creatine transporter deficiency", Nanomedicine, vol. 10, pages 185-191.

[13] Patent application EP 0 589 843 in the name of Sandoz A G, published on Mar. 30, 1994.

[14] Banerjee et al, 2010, "Effect of creatine monohydrate in improving cellular energetics and muscle strength in ambulatory Duchenne muscular dystrophy patients: a

[15] Balestrino et al, 2010, "Potential of creatine or phosphocreatine supplementation in cerebrovascular disease and in ischemic heart disease", Amino Acids, vol. 48, pages 1955-1967.

[16] Luiz Fernando Freire Royes & Cassol, 2016, "The effects of creatine supplementation and physical exercise on traumatic brain injury", Mini Rev Med Chem, vol. 16, pages 29-39.

[17] Brewer & Wallimann, 2000, "Protective effect of the energy precursor creatine against toxicity of glutamate and beta-amyloid in rat hippocampal neurons", J Neurochem, vol. 74, pages 1968-1978.

[18] Lensman et al, 2006, "Intracerebroventricular administration of creatine protects against damage by global cerebral ischemia in rat", Brain Res, vol. 1114, pages 187-194.

[19] Chaturvedi & Beal, 2008, "Mitochondrial approaches for neuroprotection", Ann N Y Acad Sci, vol. 1147, pages 395-412.

[20] Abou-Sleiman et al, 2006, "Expanding insights of mitochondrial dysfunction in Parkinson's disease", Nat Rev Neurosci, vol. 7, pages 207-219.

[21] Matthews et al, 1999, "Creatine and cyclocreatine attenuate MPTP neurotoxicity", Exp Neurol, vol. 157, pages 142-149.

[22] Adhihetty et al, 2008, "Creatine and its potential therapeutic value for targeting cellular energy impairment in neurodegenerative diseases", Neuromolecular Med, vol. 10, pages 275-90.

[23] Hersch et al, 2006, "Creatine in Huntington disease is safe, tolerable, bioavailable in brain and reduces serum 8OH2" dG", Neurology, vol. 66, pages 250-252.

[24] Allen, 2012, "Creatine metabolism and psychiatric disorders: Does creatine supplementation have therapeutic value?", Neurosci Biobehav Rev, vol. 36, pages 1442-1462.

[25] Ipser et al, 2012, "1H-MRS in autism spectrum disorders: a systematic meta-analysis", Metab Brain Dis, vol. 27, pages 275-287.

[26] Hoerst et al, 2010, "Metabolic alterations in the amygdala in borderline personality disorder: a proton magnetic resonance spectroscopy study", Biol Psychiatry, vol. 67, pages 399-405.

[27] Bender et al, 2008, "Creatine improves health and survival of mice", Neurobiol Aging, vol. 29, pages 1404-1411.

[28] Skelton et al, 2011, "Creatine transporter (CrT; Slc6a8) knockout mice as a model of human CrT deficiency", PLoS ONE, vol. 6, e16187.

The invention claimed is:

1. A composition for use in medicine, said composition comprising at least one creatine fatty ester or salt thereof in an amount of 0.01% to 6% by weight based on the total weight of the composition, at least one omega 3 fatty acid or salt thereof in an amount of 15% to 35% by weight based on the total weight of the composition and at least one glyceride in an amount of 60% to 85% by weight based on the total weight of the composition, said composition being free of non ionic surfactants.

2. The composition according to claim 1, wherein said creatine fatty ester is represented by the formula (I):

$$(NH_2)-C(NH)-N(CH_3)-CH_2-COOR \qquad (I)$$

in which R represents an alkyl radical with 4 to 30 carbon atoms, an alkenyl radical with 4 to 30 carbon atoms or an aryl radical with 6 to 30 carbon atoms.

3. The composition according to claim 1, wherein said creatine fatty ester or salt thereof is dodecyl creatine ester or hydrochloride salt of dodecyl creatine ester.

4. The composition according to claim 1, wherein said at least one creatine fatty ester or salt thereof is present in an amount of 0.02% to 5.5% by weight based on the total weight of the composition.

5. The composition according to claim 1, wherein said at least one omega-3 fatty ester or salt thereof is docosahexaenoic acid (DHA).

6. The composition according to claim 1, wherein said at least one omega-3 fatty ester or a salt thereof is present in an amount of 20% to 30% by weight based on the total weight of the composition.

7. The composition according to claim 1, wherein said at least one glyceride is a mixture of mono-, di- and triglycerides of linoleic ($C_{18:2}$) and oleic ($C_{18:1}$) acids.

8. The composition according to claim 1, wherein said at least one glyceride is present in an amount of 70% to 80% by weight based on the total weight of the composition.

9. The composition according to claim 1, wherein said composition is prepared by a method comprising a step consisting in mixing at least one creatine fatty ester or salt thereof, at least one omega 3 fatty acid or salt thereof and at least one glyceride.

10. The composition according to claim 1, wherein said composition is for use in the treating or the preventing of at least one disease, disorder or condition selected in the group consisting of a neuromuscular disorder, hypoxia, an ischemic brain disease, an heart disease, a muscular dystrophy, a skin disorder, a neurodegenerative disease, leukodystrophy, a psychiatric disorder, and inflammation and wherein said composition is suitable for nasal administration.

11. The composition according to claim 1, wherein said composition is for use in treating brain creatine transporter deficiency disease and wherein said composition is suitable for nasal administration.

12. The composition according to claim 1, wherein said composition is suitable for nasal administration.

13. The composition according to claim 1, wherein the composition is for use in treating or preventing an ageing-related condition.

* * * * *